(12) United States Patent
Roof et al.

(10) Patent No.: US 6,905,840 B1
(45) Date of Patent: Jun. 14, 2005

(54) DOUBLE MOTOR MUTANT ASSAY FOR ANTIFUNGAL AGENTS

(75) Inventors: David M. Roof, San Carlos, CA (US); Mary Maxon, San Francisco, CA (US)

(73) Assignee: Cytokinetics, Inc., South San Francisco, CA (US)

(*) Notice: Subject to any disclaimer, the term of this patent is extended or adjusted under 35 U.S.C. 154(b) by 0 days.

(21) Appl. No.: 10/414,270

(22) Filed: Apr. 14, 2003

(51) Int. Cl.$^7$ .............. C12Q 1/16; C12Q 1/68; C12Q 1/48; C12Q 1/02
(52) U.S. Cl. ............... 435/32; 435/6; 435/15; 435/29
(58) Field of Search ............... 435/32, 6, 15, 435/29

(56) References Cited

U.S. PATENT DOCUMENTS 5,418,144 A * 5/1995 Kirsch et al. .............. 435/32

OTHER PUBLICATIONS

DeZwann, et al., "Kinesin–related KIP3 of *Saccharomyces cerevisiae* Is Required for a Distinct Step in Nuclear Migration", The Journal of Cell Biology, vol. 138, 1997, pp. 1023–1040.

* cited by examiner

*Primary Examiner*—Kent Bell
(74) *Attorney, Agent, or Firm*—Beyer Weaver & Thomas LLP

(57) ABSTRACT

Provided are methods of identifying potential antifungal agents, and particularly those having antimitotic activity. Fungal cells having double mutations which alter microtubule stability and inhibit cell proliferation are used in the methods. Test compounds are screened to identify those which are able to promote cell proliferation o the mutant fungal cells and counteract the stabilizing effect of the double mutations on the microtubules. High-throughput methods of selecting for the novel antifungal agents are also provided.

70 Claims, 1 Drawing Sheet

DOUBLE MOTOR MUTANT ASSAY FOR ANTIFUNGAL AGENTS

BACKGROUND OF THE INVENTION

1. Field of the Invention

This invention pertains to the fields of antifungal therapeutics and drug discovery. More specifically, the invention pertains to the use of fungal mutations affecting microtubule stability to identify compounds suitable as antifungal agents.

2. Description of Related Art

The incidence and severity of fungal infections have increased greatly over recent years. Fungal infections of particular concern in recent times include aspergillosis (infection by *Aspergillus* sp., such as *Aspergillus fumigatus*), cryptococcosis (infection by *Cryptococcus neoformans*), zygomycosis (infection by zygomycetes), and candidiasis (infection by *Candida* sp.). Some of these fungal infections, such as disseminated aspergillus, disseminated cryptococcosis, and zygomycosis, are frequently fatal, especially in a debilitated patient. Furthermore, some fungal infections, such as candidiasis and cryptococcosis, are extremely common in aids patients Current antifungal therapies typically employ amphotericin B, 5-flucytosine, caspofungin, and/or various azole derivatives such as fluconazole, ketoconazole, and itraconazole. No known form of therapy is effective on all fungal infections, and all of the known therapies carry with them some level of human toxicity. Increasing levels of resistance to known therapies also present a problem. Despite efforts to minimize toxicity and maximize potency of the azoles since the 1970s, amphotericin B, a drug introduced in the 1950s, remains the best choice for many serious mycoses, and, in particular, disseminated mycoses, despite the drug's significant toxicity and problems with resistance and non-availability of an absorbable oral form for long-term maintenance. Attempts to encapsulate amphotericin B into liposome vesicles to diminish toxicity have proven only moderately successful.

During mitosis, the mitotic spindle undergoes a complex series of transitions. At each mitotic cell division, the spindle assembles, forms attachments to the chromosomes, orients itself properly within the cell, and carries out chromosome segregation, before disassembling again. Proper spindle assembly and function involves coordination of many cellular events including the creation and control of at least three distinct types of microtubules: kinetochore, polar, and astral microtubules. Microtubules mediate a series of movements that culminate in chromosome segregation, including migration of the nucleus to the neck between the mother and daughter cells, assembly of a bipolar spindle, translocation of the spindle through the neck, and elongation of the spindle. This set of molecular events results in chromosome to pole movement (anaphase a) and separation of spindle poles (anaphase b).

As cells enter mitosis, cytoplasmic microtubules depolymerize and the mitotic spindle forms. During mitosis, the dynamic spindle microtubules undergo specific depolymerization events. Perturbing either the depolymerization or polymerization of microtubules in mitosis, either with drugs or by genetic lesions, interferes with mitotic progression, sometimes leading to arrest in proliferation.

Some agricultural fungicides have also been reported as having antimitotic modes of action. For instance, benomyl, a major agricultural fungicide, acts as a microtubule destabilizer in fungi. Similarly acting compounds include carbendazim (an active breakdown product of benomyl), and thiabendazole (an agricultural and veterinary fungicide). However, these fungicides are generally not very specific. Furthermore, the potential health hazards of some of these fungicides, such as benomyl, have created concern and are the target of investigations (see, e.g., Watterson, *J. of Public Health Medicine*, 16:141–144(1994).

Accordingly, the discovery of antifungal agents with novel mechanisms of action would be highly desirable.

SUMMARY OF THE INVENTION

This invention provides a method for identifying compounds with potential antifungal activity and, in particular, compounds which disrupt fungal mitosis by altering the stability of fungal microtubules. The method utilizes fungal double mutants having hyper-stable microtubules to screen for agents with microtubule-destabilizing activity.

In one aspect, the invention pertains to a method for identifying a compound having antifungal activity. The method involves screening the test compound for its apparent ability to stabilize microtubules. The method includes the following: providing a population of double mutant fungal cells, the cells having genetic mutations of at least a first and a second gene wherein (1) the genes encode motor proteins that have antagonistic and complementary functions; (2) the mutation of said first gene or said second gene results in loss of function of the protein encoded thereby, but does not prevent cellular proliferation; (3) mutation of said first and second genes results in the loss of function of both proteins encoded thereby and prevents proliferation under restrictive conditions; and (4) contact of the double mutant fungal cells with an agent results in proliferation under restrictive conditions. The population is contacted with a test compound under conditions under which proliferation of the population of fungal cells would be prevented due to the mutations in the absence of the test compound (i.e., restrictive conditions). Then it is determined whether the test compound allows proliferation to occur so as to identify a test compound that allows proliferation to occur as a compound having potential antifungal activity. Proliferation of the mutant cells indicates that the test compound relieves the effects of the mutation and is a potential antifungal agent.

The method may additionally include treating a second population of fungal cells without the mutations with the test compound. If the test compound also inhibits growth of these normal fungal cells, then the test compound is determined to be an antifungal agent.

Preferably, the second population of fungal cells is the same species as the mutant fungal cells, although alternative embodiments of the method a second population of fungal cells that is a different species from the mutant fungal cells.

The method also comprises testing plant and/or animal cells with the potential antifungal agent to determine if the antifungal agent is toxic to potential host organisms for therapeutic or agricultural applications.

Such mutations are most preferably in fungal cells from *Saccharomyces, Aspergillus, Histoplasma, Cryptococcus*, or *Candida* sp. The mutations hyper-stabilize the microtubules. Most preferably, these mutations are in the *Saccharomyces cerevisiae* KIP3 (GenBank accession number Z72739, open reading frame YGL216c) and KAR3 (GenBank accession number M31719) or DYN1 (GenBank accession number Z21877), or KAR3 and DYN1 genes, or a homologue of the same.

Restrictive conditions of the invention preferably are based on temperature. Temperature leading to restrictive growth are most preferably above 30° C., for example about 37° C.

Preferable techniques for detecting cell proliferation include absorbance spectrophotometry, fluorescence spectroscopy, fluorescence microscopy, epifluorescence microscopy, light microscopy, phosphorimaging and nephelemetry, techniques that use dyes that change color or fluoresce upon metabolism and techniques that measure $O_2$ consumption. Cells are preferably stained with a fluorogenic compound, a naturally fluorescent compound, a calorimetric compound, a chemiluminescent compound, a radioactive compound or combinations thereof to aid detection. A particularly preferred stain is the fluorescent dye, Calcofluor white.

An alternative embodiment of the present invention involves comparing the effect of a test compound on mutant cell growth to that of a known microtubule destabilizer. This typically involves incubation of cells in the presence of the test compound while incubating identical cells in the presence of the known microtubule destabilizer in a parallel assay. The growth in the presence of the test compound is then compared to the growth in the presence of the known microtubule destabilizer. This comparison of relative growth rates allows for the effectiveness of the test compound as an agent affecting microtubule stability to be ascertained. Microtubule destabilizer used in the invention are preferably nocodazole-like compounds, most preferably benomyl.

The detecting device used in the present methods can be a microscope, a photodiode, a Geiger-Mueller tube, a fluorometric detector, a spectrophotometric detector, or a combination of any of the above.

These and other features and advantages of the present invention are described below where reference to the drawings is made.

DETAILED DESCRIPTION OF SPECIFIC EMBODIMENTS

Figure 1A:
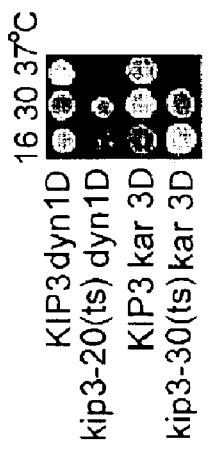
FIGS. 1A–C depict aspects of procedures used to identify and characterize conditionally lethal kip3/dyn1, kip3/kar3 and kar3/dyn1 double mutants.

Reference will now be made in detail to specific embodiments of the invention. Examples of the specific embodiments are illustrated in the accompanying drawings. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

When used in combination with "comprising," "a method comprising," "a device comprising" or similar language in this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Introduction

The use of, and need for antifungal agents is widespread and ranges from the treatment of mycotic infections in animals; to disinfectant formulations; to pharmaceuticals for human use. A major problem with current antifungal formulations is their toxicity to the infected host. This is particularly important in human beings where many fungal infestations are advantageous secondary infections to debilitating diseases, such as AIDS or from chemotherapy or transplants. Correspondingly, at least for antifungal agents that are to be administered to humans and other animals, the therapeutic index is preferably such that toxicity to the host is several orders of magnitude less than it is for the targeted fungus.

The present invention relates to reliable and effective assays for screening and identifying effective antifungal compounds that specifically inhibit microtubule function, thereby preventing fungal growth and killing the infectious agent. By compromising microtubule function, compounds identified by the present invention disrupt mitosis, hyphael formation, cellular transport mechanisms and other cellular functions critical to pathogenesis.

The present invention uses double mutant fungal strains that are deficient in ways relating to bio-formation of microtubules. Such mutants typically are conditional in nature, displaying a scoreable phenotype, such as growth arrest (failure to proliferate), in response to particular environmental (restrictive) conditions. Primary assays involve treating such mutants with test compounds under restrictive conditions to identify those compounds capable of relieving the scoreable phenotype by compensating for the mutation affecting microtubule formation. Such compounds themselves must necessarily be impacting microtubule formation to reverse the mutant phenotype and are marked as potential antifungal agents deserving further study.

Compounds identified in primary assays as potential antifungal agents may be investigated further to determine their efficacy as fungicides. These secondary assays employ wild-type fungal strains and directly test identified compounds for their effects on fungal growth. Preferably identified compounds are cytotoxic. Identified compounds proving to be toxic to wild type fungal strains are labeled as antifungal.

Antifungal compounds are further tested for potential toxic effects on projected host organisms, such as animals or plants. Ideally, toxicity toward the host organism is several orders of magnitude lower than toxicity toward fungi.

In addition to methods for identifying effective antifungal compounds, the present invention also provides methods for comparing the efficacy of such compounds.

In one embodiment, this invention provides a method for identifying a compound having potential antifungal activity. The method involves screening the test compound for its apparent ability to destabilize microtubules. The method includes the following steps: providing a population of double mutant fungal cells, the cells having genetic mutations of at least a first and a second gene wherein (1) the genes encode motor proteins that have antagonistic and complementary functions, (2) the mutation of said first gene or said second gene results in loss of function of the protein encoded thereby, but does not prevent cellular proliferation, and (3) mutation of said first and second genes results in the loss of function of both proteins encoded thereby and prevents proliferation under restrictive conditions, and (4) contact of the double mutant fungal cells with an agent results in proliferation under restrictive conditions; contacting the population with a test compound under conditions under which proliferation of the population of fungal cells would be prevented due to the mutations in the absence of the test compound (i.e., restrictive conditions); determining whether the test compound allows proliferation to occur so as to identify a test compound that allows proliferation to occur as a compound having potential antifungal activity. Where the mutations result in hyper-stable microtubules, the test compounds identified as potential antifungal agents by this technique are potential microtubule destabilizers.

Determining whether cell proliferation occurs in the presence of a test compound can be made using methods such as spectrophotometry, fluorescence spectroscopy, and fluorescence microscopy. For instance, growth of a fungus like *Saccharomyces Aspergillus, Histoplasma, Cryptococcus*, or *Candida* sp. can be monitored spectrophotometrically or microscopically using imaging technology. To aid the monitoring of proliferation of the fungal cells, a cell wall stain, such as Calcofluor white (Fluorescence Brightener 28 from Sigma) or fluorescent concanavalin A; or a vital stain such as FUN-1 (Molecular Probes, Inc.); or an internal fluorescent marker such as GFP can optionally be used. Calcofluor white can be used to stain the fungal cells and fluorescence spectroscopy or microscopy is used to detect cell proliferation. Calcofluor white and fluorescence spectroscopy or microscopy are especially preferred when a high-throughput screening system is in use.

Optionally, the steps of the method for identifying compounds having potential antifungal activity can be repeated with a second population of fungal cells. The second population of fungal cells differs in species or genus from the first population and has genes homologous to the mutated genes of the first population, the homologous genes comprising analogous mutations. For instance, if the first population comprises *Saccharomyces cerevisiae* having mutant KIP3 and DYN1 which stabilizes microtubules, then the second population might optionally comprise *Aspergillus, Cryptococcus, Histoplasma*, or *Candida* sp. or any other genetically manipulatable fungi into which the analogs of the KIP3 and DYN1 mutations have been genetically engineered. Preferably, the screening of test compounds using the first population and the second population are carried out in parallel.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

"Fungal cells" are cells derived from any member of the fungal kingdom. The cells may be naturally occurring or, alternatively, may be transgenic or recombinant. For example, fungal cells may be derived from *Aspergillus, Saccharomyces, Cryptococcus, Histoplasma*, or *Candida*. A "population of fungal cells", "population", and "cell population" refer to a plurality of fungal cells.

A "test compound" or "test agent" is any compound or agent that is desirably screened for potential antifungal and/or antimitotic activity. The terms "compound" and "agent" are used interchangeably herein. A "compound" can be either a single molecule or a multi-molecular complex. A compound is optionally selected from the group consisting of a small organic molecule, an organometallic molecule, a modified nucleic acid molecule, a small peptide, polynucleotide, or a protein. Most commonly, the compound will be a small organic molecule (e.g., having a molecular weight (MW) of about 200 to 1000 Daltons, preferably about 300–800 Daltons. A test compound used in the methods of the invention is preferably a member of a library of different compounds. The library optionally has been derived from any synthetic or combinatorial method known to those of ordinary skill in the art. Alternatively, the library has been isolated from natural sources. The identity or composition of a test compound need not necessarily be known at the time the screen for antifungal activity is initiated. The identity of the test compound can optionally be determined once potential antifungal activity has already been established.

The term "antifungal" as used in conjunction with the terms "agent" or "activity" indicates that the agent or activity diminishes the viability, growth, and/or reproduction of fungal cells. In some cases, an antifungal is a broad spectrum antifungal. However, an antifungal agent or activity can instead be specific to one or more particular fungi. The antifungal agent or activity can be active against any combination of the following fungi: *Aspergillus fumigatus; Candida albicans; Cryptococcus neoformans; Cryptococcus albidus; Cryptococcus laurentii; Aspergillus flavus; Aspergillus nidulans; Aspergillus niger; Aspergillus terreus; Candida krusei; Candida glabrata; Candida guilliermondii; Candida parapsilosis; Candida tropicalis; Candida pseudotropicalis; Absidia corymbifera; Rhizopus oryzae; Coccidioides immites; Histoplasma capsulatum; Fusarium sp; Paracoccidiodes brasiliensis*; and *Mucor pusillus*.

A "mutation" is any modification of the wild type nucleotide sequence of a gene including partial or complete removal of the sequence (deletion).

A mutation that "affects the stability of the microtubules of the fungal cells" is a mutation that hyper-stabilizes the microtubules.

A "microtubule stabilizer," or a mutation(s) or compound that "stabilizes microtubules" or that is "microtubule stabilizing," has the effect (under at least some conditions) of increasing the presence and/or stability of microtubules of fungal cells so that the normal progression of mitosis in the fungal cells is at least partially disrupted or hindered. For instance, in some cases, a microtubule stabilizer promotes polymerization of tubulin into microtubules. Alternatively, a microtubule stabilizer can inhibit depolymerization of the microtubules. It is also possible that the same agent or mutation would have both effects under different circumstances. The stabilizing effect on the microtubules can be due to a direct interaction of the test compound with the tubulin of the fungal cells, but need not necessarily be so. The effect can instead be indirect (for instance, due to the stimulation of expression of a cell product which stabilizes microtubules). Examples of known microtubule stabilizers include Taxol®. Examples of mutations in fungal cells that stabilize microtubules include benA33, a mutation reported in *Aspergillus nidulans* (Jung et al., *Fungal Genetics and Biology*, 24: 146–160 (1998)) and tub2-150, which has been reported in *Saccharomyces cerevisae* (Machin et al., *Molecular Biology of the Cell*, 6:1241–1259 (1995)). Other examples include, but are not limited to, the following A. nidulans alleles: ben11; benA17; benA21; benA31; and benA32 (Jung et al., *Fungal Genetics and Biology*, 24: 146–160 (1998)).

A "microtubule destabilizer," or a mutation(s) or compound that "destabilizes microtubules" or that is "microtubule destabilizing," has the effect (under at least some conditions) of decreasing the presence and/or stability of microtubules of fungal cells so that the normal progression of mitosis in the fungal cells is at least partially disrupted or hindered. For instance, some microtubule destabilizers inhibit polymerization of tubulin into microtubules. Alternatively, some microtubule destabilizers promote depolymerization of the microtubules. It is also possible that the same agent or mutation could have both effects in different circumstances. The destabilizing effect on the microtubules can be due to a direct interaction of the test compound with the tubulin of the fungal cells. The effect can instead be indirect (for instance, the agent may stimulate expression of a cell product which destabilizes microtubule formation). Examples of known microtubule destabilizers include benomyl, carbendazim, nocodazole, vinblastine, vincristine, tubuzole, and griseofulvin. An example of a mutation that has a microtubule destabilizing effect is tubA4 of *Aspergillus nidulans* (Oakley et al., *Mol. Gen. Genet.,* 208:135–144 (1987)).

"Hyper-stable microtubules" are microtubules in fungal cells, where the microtubules have been so stabilized by exogenous entities or by a mutation in the fungal cells themselves that progression of mitosis in those fungal cells is at least partially disrupted or hindered.

"Conditions under which proliferation of the population of fungal cells would be prevented due to the mutations" are conditions under which the fungal cells having genes comprising particular mutations that affect fungal microtubule stability fail to proliferate to any substantial degree. Preferably, under the conditions, the fungal cells fail to proliferate at all (i.e., the mutations, under these conditions, are lethal). The conditions can include the use of specific temperatures or specific media. Preferably, the conditions are such that when a microtubule destabilizer is contacted with the mutant fungal cells (whichever is appropriate to counteract the particular mutation of the fungal cells), proliferation of the fungal cells is no longer prevented. The appropriate conditions generally depend on both the particular mutation used in the screening methods and also the type of fungus from which the fungal cells are derived.

The terms "cell proliferation" or "proliferation" mean growth and/or reproduction of a population of fungal cells. To "proliferate" means to grow and/or reproduce.

Screening Test Compounds for Potential Antifungal Activity

This invention provides novel methods of identifying and further characterizing potential antifungal agents. In general, antifungal agents are initially identified based on their ability to destabilize fungal microtubules. Further characterization involves testing initially identified antifungal agents for cytotoxic effects on one or more fungal strains. Antifungal agents are also screened for their toxicity to animals and plants, particularly humans and crop plants.

Primary Screening Assays

A compound with potential antifungal properties is identified in primary screening by treating fungal cells carrying a conditional double mutation affecting microtubule stability (e.g., hyper-stabilizing microtubules) with the compound under the restrictive conditions. Compounds which permit the mutant cells to grow must themselves affect microtubule stability (e.g., destabilize microtubules) in the mutant by reversing the effects of the microtubule stability double mutation. Such compounds have the potential to alter microtubule stability in wild-type fungi thereby affecting fungal proliferation, and are marked for further study. The compound permitting mutant cells to grow may be further characterized in secondary screening tests.

The Fungi

The fungal cells used in screening methods of the present invention can be cells derived from any fungi. For instance, the cells can be *Aspergillus, Saccharomyces, Cryptococcus, Histoplasma,* or *Candida,* such as *Saccharomyces cerevisae* cells, *Aspergillus nidulans* cells, or *Candida albicans* cells. In a preferred embodiment, the fungal cells used in the methods are *Saccharomyces cerevisae* cells.

Fungal cells can be naturally occurring. Alternatively, the fungal cells may be transgenic or recombinant. The recombinant fungal cells may contain portions of gene sequence or mutations that are heterologous to the fungus from which the cells were primarily derived. In some cells for instance, one or more tubulin-related genes of the fungal cells is heterologous to the rest of the fungal genome. In some cells a mutation previously identified in one fungus may be genetically engineered into the genome of fungal cells from a different fungus.

The antifungal activity of a test compound identified in a primary screening test as a potential antifungal agent is not necessarily specific to the fungus used in the primary screening. Such a compound can be an effective antifungal agent against a specific fungus, family of fungi or all members of the class. Thus in one embodiment, the specific fungal strains susceptible to the test compound are determined by applying the compound to a number of fungal strains in the secondary screening test. The fungal strains used in the secondary screening test may or may not include a mutation-free version of the strain used in the primary screening.

Other embodiments of the invention may utilize the same or a different fungus used in the primary screening stage in one or more secondary screening stages. Further screening stages may utilize different fungi (e.g., if *Saccharomyces cerevisae* cells are used for the primary and/or secondary assays, *Aspergillus nidulans* cells, or *Candida albicans* cells may be used in such a further screen) or cells of other organisms, such as plant and animals in order to ascertain the generality of effect of the antifungal agent and potential host toxicity.

The Mutations

The fungal cells used in the primary screening methods typically have at least a pair of genes comprising mutations that affect microtubule stability, resulting in hyper-stable microtubules. The two or more mutated genes code for proteins in balance so that a mutation to either gene resulting in the loss of its protein's function would not prevent proliferation (e.g., would not be lethal), but the loss of both genes would prevent proliferation (e.g., would be lethal) under certain (e.g., restrictive) conditions.

Such fungal double mutations that cause hyper-stable microtubules are known. As described in DeZwaan, T. M., E. Ellington, D. Pellman, D. M. Roof. 1997. Kinesin-related KIP3 of *Saccharomyces cerevisiae* Is Required for a Distinct Step in Nuclear Migration, *J. Cell Biol.* 138: 1023–1040, the disclosure of which is incorporated by reference herein in its entirety for all purposes, movements in *Saccharomyces cerevisiae* that culminate in chromosome segregation have been associated with the action of particular microtubule-based motor proteins by examining mutants defective in motor function and identifying the perturbed movement.

The completed DNA sequence of the *S. cerevisiae* genome has revealed the complete set of kinesin-related proteins in this eukaryote. A *S. cerevisiae* protein with substantial homology to the force-generating domain of kinesin, named Kip3p, is required for the first phase of nuclear migration: alignment of the mitotic spindle along the mother-daughter axis and movement of the preanaphase nucleus to the bud neck. Loss of the KIP3 gene function disrupts the unidirectional movement of the nucleus toward the bud and mitotic spindle orientation, causing large oscillations in nuclear position. The kip3 null mutant produces normal (wild type) tubulin, exhibits normal translocation of the nucleus through the neck and normal spindle pole separation kinetics during anaphase, and is viable. The oscillatory motions sometimes bring the nucleus in close proximity to the bud neck, possibly accounting for the null mutant's viability.

Dynein has been implicated in generating forces for spindle pole separation during anaphase B, along with the kinesin-related proteins Kip1p and Cin8p (Saunders, W. S., D. Koshland, D. Eshel, I. R. Gibbons, and M. A. Hoyt. 1995. *Saccharomyces cerevisiae* kinesin- and dynein-related proteins required for anaphase chromosome segregation. *J. Cell Biol.* 128: 617–624; Yeh, E., R. V. Skibbens, J. W. Cheng, E. D. Salmon, and K. Bloom. 1995. Spindle dynamics and cell cycle regulation of dynein in the budding yeast, *Saccharomyces cerevisiae*. *J. Cell Biol.* 130: 687–700). Kinetic analysis of spindle pole separation in live cells has shown that loss of dynein function slows the rate of spindle pole separation in late anaphase (Yeh et al., 1995). Analysis of populations of fixed cells has shown that loss of Kip1p and Cin8p function abolishes pole separation during spindle assembly and causes an inward collapse of metaphase spindle poles (Hoyt, M. A., L. He, K. K. Loo, and W. S. Saunders. 1992. Two *Saccharomyces cerevisiae* kinesin-related gene products required for mitotic spindle assembly. *J. Cell Biol.* 118: 109–120; Roof, D. M., P. B. Meluh, and M. D. Rose. 1992. Kinesin-related proteins required for assembly of the mitotic spindle. *J. Cell Biol.* 118: 95–108; Saunders, W. S., and M. A. Hoyt. 1992. Kinesin-related proteins required for structural integrity of the mitotic spindle. *Cell.* 70: 451–459).

Mutations in another kinesin-related motor protein, Kar3p, can suppress the spindle collapse caused by loss of Kip1p and Cin8p function. This suggests that Kar3p contributes to a force that opposes an outwardly directed force on the spindle poles generated by Kip1p and Cin8p (Hoyt, M. A., L. He, L. Totis, and W. S. Saunders. 1993. Loss of function of *Saccharomyces cerevisiae* kinesin-related CIN8 and KIP1 is suppressed by KAR3 motor domain mutations. *Genetics*. 135; 35–44).

Loss of dynein function has little effect on preanaphase nuclear migration and spindle orientation and loss of KIP3 function has little effect on movement of the anaphase nucleus through the bud neck. Kip3p is located on both astral and nuclear microtubules at all stages of the cell cycle. Kip3p is essential in strains lacking kinesin-related Kar3p and in strains lacking dynein heavy chain, indicating that Kip3p performs overlapping or dependent functions with Kar3p and dynein. Simultaneous loss of KIP3 and kinesin-related KAR3 function, or of KIP3 and dynein function, is lethal but does not block any additional detectable movement. KAR3 and DYN1 double mutants are also lethal. This suggests that the lethality is due to the combination of sequential and possibly overlapping defects of the mutated genes.

Some methods of the invention use mutations identified in one fungus and engineered into another organism for use in primary screenings of the present invention. For instance, the kip3 and kar3 or dyn1 mutation analogs can be engineered into a fungus other than *Saccharomyces cerevisae*, such as *Aspergillus* or *Candida* sp., and the resulting fungal cells used to identify agents which have potential microtubule destabilizing activity and potential antifungal activity. Methods of introducing appropriate point mutations into fungi are well known and involve transformation procedures that exploit homologous recombination to precisely position modified genes into a host genome. (see, e.g., P. T. Magee, *Methods in Microbiology*, 26:395–415 (1998)).

Strains described herein with additional mutation(s) in drug efflux pump(s), such as are known on the art (e.g., as described in U.S. Pat. No. 6,495,591 and references cited therein) may also be used to expand the range of sensitivity of methods in accordance with the present invention.

Restrictive Conditions

Preferably, the conditions used in the methods are such that the microtubule-stabilizing mutations prevent proliferation of the fungal cells from occurring in the absence of a microtubule destabilizer. These conditions will vary depending upon the fungi and the mutations used. For instance, when the fungal cells are *S. cerevisae* and the mutations are in KIP3 and DYN1 or KAR3, preferred conditions include standard *S. cerevisae* media and an incubation temperature above 30° C., for example 37° C., for about three days (about 60 to about 80 hours). Of course, one of skill in the art would be able to modify media, temperature, conditions, etc. to achieve optimal signal to noise. Preferably the mutant fungal cells are not viable under the conditions used unless a microtubule destabilizer is added.

Media used in the primary screening assay methods can be of any type which allows growth of the mutant fungi in the presence of compounds relieving the mutant phenotype being monitored. In this regard, suitable controls carried out in the absence of any test compound are a routine aspect of the present invention.

Secondary Screening Assays

Secondary screening assays can be performed with any type of fungi. Preferably, the fungi are of a wild type (found in nature), closely approximating to, if not identical with, the target fungi of the antifungal agent sought. Although preferably of the same genus and species as the fungi used in the primary screening assay, fungi used in the secondary screening assay may be diverse from that used in the primary screening assay. For example, the fungal strain utilized in the primary screening assay may be *Saccharomyces cerevisae*, with the identified potential antifungal compounds being tested in a secondary assay against cells, *Aspergillus nidulans*, or *Candida albicans*. Methods using this "mixed assay" approach are highly beneficial as they allow the practitioner to utilize the best strain available for the primary screening step, while retaining the capability of finding effective antifungal agents against virtually any fungal strain. Such "mixed assay" techniques are particularly powerful when coupled with the construction of chimeric fungal strains as described supra. In some secondary screening methods of the present invention, the fungal strain(s) are mutant in that they are resistant to some environmental variable, antifungal treatment or combination of the same. Use of resistant strains in these methods allows for selection of antifungal compounds to which the resistant strains are susceptible. These methods can be readily tailored to particularly refractive strains, enhancing the clinical or agricultural utility of the invention.

Media used in secondary screening assays is preferably of a "rich" type containing all carbon, nitrogen and mineral sources required by the fungi for normal growth. An important aspect is that any media type can be used, provided that it is of such content as to sustain growth of the test fungal strain(s). Other environmental parameters affecting growth, including temperature, pH, and humidity may take any value compatible with fungal growth.

Screening for Toxicity in Plants and Animals

A beneficial aspect of the approach taken in the present invention is that identified antifungal compounds may be less toxic to many species than currently available fungicides. For example, phylogenetic analysis of tubulin family homologues indicates considerable divergence between fungi and animals, man, and many plants. Consequently, compounds affecting fungal microtubule structure may have little or no effect on other species. Similar selection advantages can be found in compounds identified by the present invention affecting other aspects of fungal growth. The principal criterion in designing the method is identifying a gene coding for a protein essential to some aspect of fungal survival, which has sufficient sequence diversity from homologues found in other genera, particularly that of the target host. The ability to identify antifungal agents which are less toxic to the host organism specifically, and the environment in general, is extremely advantageous both in the clinical and agricultural setting. (For a comparative analysis of tubulin sequences from different organisms, see Little et al., *Comp. Biochem. Physiol. B,* 90:655–70 (1988), which reports that the amino acid sequence identity between *S. cerevisiae* β-tubulin and mouse β-tubulin is only 63.3%.)

The present invention also comprises characterizing identified compounds for toxic effects in plants and animals (e.g., mammals). These toxicity studies may comprise cell lines, permanent or primary, or testing in whole organisms.

Implementation

Assays in accordance with the present invention may be implemented in a variety of ways. One preferred implementation allows a plurality of test compounds to be evaluated in parallel. The method of the present invention may be performed within standard multi-well assay plates. Thus, a plurality of test compounds can be simultaneously screened.

As would be apparent to one of skill in the art from the disclosure of the present invention, it is also contemplated that the methods of the present invention may be performed in a cell-based, in vitro reaction. Exemplary cell-based, in vitro platforms suitable for modification in accordance with the method of the present invention are described in Parkinson, Toxicol. Pathol. 24:45–57 (1996). As would also be apparent to one of skill in the art from the disclosure of the present invention, any method capable of detecting sporulation, proliferation or the presence of hypha including light, phase contrast and fluorescent microscopy; absorbance, fluorescent, and nephelometric spectroscopy; calorimetric assays; and incorporation assays, provides a suitable detection method for the present invention. For example, Calcofluor White is an indicator compound capable of staining fungal cell walls, aiding in detection of fungal proliferation.

In a preferred embodiment of the invention, the methods used to identify the potential antifungal agents are high-throughput assays. Such high-throughput assays typically involve the repeating of the steps of the methods in parallel to screen a large number of test compounds for potential antifungal activity and/or host effects. Typically, these steps are automated and computer-controlled.

For example, steps of the methods are optionally performed in a high-throughput integrated system which includes a detection system suitable for the high-throughput measuring of a fungal cell population at an assay site following contact of the fungal cells with a test compound. The high throughput system for automated detection includes a data storage unit to record the detection readings. Detection of fungal cell proliferation and growth is optionally performed in a high-throughput integrated system that includes a spectrophotometer or a fluorescence plate reader with cells optionally stained for ease of detection. In a particularly preferred embodiment, Calcofluor white is used as a cell-wall stain and the amount of cell proliferation is detected using a fluorescence plate reader. The integrated system can also include a device that transfers a stain that aids in detection of the fungal cells to the assay site in an automated fashion. For instance, the size of a cell population can be determined in an automated manner using Calcofluor white as a stain and an automated microtiter plate handling and dispensing system like PlateTrak™ (CCS Packard, Torrance, Calif.). The fluorescent signal can optionally be read using an automated microplate-based fluorescence reader like POLARStar™ Galaxy from BMG Labtechnologies (Offenburg, Germany).

All alternative detection techniques disclosed in this application may be automated through the use of suitable robotics and computer interfaces.

Pharmaceutical Preparations of Identified Antifungal Compounds

After identifying certain test compounds as potential antifungal agents, the practitioner of the methods of the present invention may continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

Other compounds identified by the present invention will prove be effective against fungal infestations of plants. Agricultural benefits of these compounds will be enhanced by incorporation of the compounds into topical formulations which are resistant to aqueous washes, allowing the compound to remain on the infected individual for a prolonged period, regardless of climactic conditions. Further enhancements can include absorption of the compound into the plant which would lead to the added advantage that deep tissue infections would also be subject to treatment. Still other formulations would enhance the foccular or dispersing properties of the compound making it more amenable to application by spraying or dusting.

Identified compounds, and derivatives thereof, may accordingly be formulated for administration with a biologically acceptable medium, such as water, buffered saline, polyol (for example, glycerol, propylene glycol, liquid polyethylene glycol and the like) or suitable mixtures thereof. Alternatively, topical suspensions may include formulation of identified compounds with talc, silicone, glycerin or other suitable carriers to aid in application or retention of the compound to the infected area or area to be protected from infection. The optimum concentration of the active ingredient(s) in the chosen medium can be determined empirically, according to procedures well known to medicinal or agricultural chemists. As used herein, "biologically acceptable medium" includes any and all solvents, dispersion media, and the like which may be appropriate for the desired route of administration of the preparation. The use of such media for biologically active substances is known in the art. Except insofar as any conventional media or agent is incompatible with the activity of the compound, its use in the biological preparation of the invention is contemplated. Suitable vehicles and their formulation inclusive of other proteins are described, for example, in the book Remington's Pharmaceutical Sciences (Remington's Pharmaceutical Sciences. Mack Publishing Company, Easton, Pa., USA 1985). These vehicles include injectable "deposit formulations". Based on the above, such biological formulations include, although not exclusively, solutions or freeze-dried powders of the compound in association with one or more biologically acceptable vehicles or diluents, and contained in buffered media at a suitable pH and, when necessary, isosmotic with physiological fluids. In preferred embodiment, the compound can be disposed in a preparation for topical and/or systemic administration.

In the case of freeze-dried pharmaceutical preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of compounds in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

EXAMPLE

Characterization of Kip3/Dyn1 and Kip3/Kar3 Double Mutants

Synthetic Lethal Interactions of the Kip3 Mutation with Mutations in other Microtubule-Based Motor Genes The phenotypes of mutants singly defective in KIP3 or DYN1 indicate that KIP3 is required for nuclear migration to the bud neck and preanaphase spindle orientation, but that DYN1 is not. However, kip3p and Dyn1p may perform overlapping or dependent functions that are not evident in the single mutants. For instance, a binucleate mother cell phenotype manifested by both kip3 and dyn1 mutants may reflect a common function in insertion of the anaphase nucleus through the bud neck. Alternatively, the cumulative effect caused by loss of the sequential migration and insertion steps of nuclear migration may be greater than that caused by loss of migration or insertion individually. Similarly, KIP3 could overlap with any of the other kinesin-related genes to perform an essential function, and this overlap would only result in a phenotype upon loss of both activities.

Synthetic phenotypes were tested by constructing double deletion mutants in the presence of a plasmid-based copy of one wild-type gene and then it was determined whether the strain remained viable after plasmid segregation (DeZwaan, et al., 1997). The kip3 dyn1, kip3 kar3, and kar3 dyn1 strains all required a complementing plasmid for viability, indicating that these combinations were synthetically lethal. The kip3 kip1, kip3 cin8, kip3 smy1, and kip3 kip2 double mutants were all viable and formed colonies equal in size to the single mutants at 16, 23, 30, and 37° C. (at 37° C. the cin8 and kip3 cin8 strains showed equally poor growth), indicating that these pairs of genes are not solely responsible for an essential function. FIG. 1A illustrates synthetic lethality of kip3, dyn1, and kar3. Strains kip3, dyn1, kar3, kip3 dyn1 (DS732), kip3 kar3 (DS716), and dyn1 kar3 (DS743) carry a centromere-based plasmid with the markers indicated in parentheses. To test whether the plasmids are essential for viability, the strains were grown on YPD medium for 3 days at 30° C. to allow for possible plasmid loss, the strains were plated on minimal medium lacking uracil (selects for plasmid) and on 5-FOA medium (selects against plasmid), and the plates were photographed after 3 days of incubation at 30° C.

Simultaneous Loss of KIP3 and Dynein, KIP3 and KAR3 or KAR3 and Dynein Function Causes Lethality To distinguish whether the kip3 and dyn1 and kip3 and kar3 double mutant mutations are synthetically lethal because of a functional overlap or due to a cumulative effect caused by partial loss of sequential functions, conditional double mutants were examined. Temperature-sensitive kip3 (ts) dyn1 and kip3-30(ts) kar3 double mutant strains were constructed by the plasmid shuffle technique (FIG. 1B: Strains dyn1 (DS749), kip3-20(ts) dyn1 (DS765), kar3 (DS750), and kip3-30(ts) kar3 (DS752) were grown to saturation and spotted on YPD medium at the indicated temperature. Plates were photographed after 7 d at 16° C. and after 3 d at 30 or 37° C.). A culture of the kip3-20(ts) dyn1 strain grown at 23° C. contained 48% inviable cells, while kip3 and dyn1 single mutant cultures contained 95–100% viable cells. Incubation of the double mutant at 37° C. for 4 h resulted in a doubling of cell number and a reduction of cell viability to 25%. Continued incubation at 37° C. resulted in a second doubling of cell number by 16 h, at which time cell number ceased to increase and cell viability remained at 25%. This suggests that the synthetic lethality is not solely due to induction of a checkpoint that arrests cell cycle progression and prevents inviability.

To determine whether KIP3 and DYN1 overlap in function for insertion of the nucleus into the neck during anaphase spindle elongation, we measured the frequency of mother cells containing two discrete nuclear DNA masses. The kip3(ts) dyn1 double mutant culture incubated at 37° C. for 4 h contained 10% binucleate mother cells, compared to 6% binucleate cells in kip3 and dyn1 single mutants. An independent kip3(ts) allele in a dyn1 strain had a similar cell type distribution. Since the double mutant culture incubated for 4 h at 37° C. still contained some anaphase cells, we examined a culture incubated for 8 h at 37° C. and found that the binucleate mother cells increased to 23%. Thus, simultaneous loss of KIP3 and DYN1 function causes defective insertion of anaphase spindles through the bud neck, in addition to causing defective preanaphase nuclear migration and a metaphase delay. This suggests that the synthetic lethality of kip3 dyn1 mutants is a cumulative effect caused by loss of partially overlapping and sequential functions.

Since one phenotype of the kip3 single mutant and the kip3(ts) dyn1 double mutant is increased microtubule abundance, it was tested whether the microtubule-depolymerizing drug benomyl could suppress the lethality of the kip3(ts) dyn1 double mutant. The double mutant showed little growth at 37° C. in the absence of benomyl but exhibited significant growth on media containing 5 or 10 $\mu$g/ml benomyl (FIG. 1C: Benomyl partially suppresses the temperature sensitivity of kip3(ts) dyn1$\Delta$ and kip3(ts) kar3$\Delta$ strains. Strains wild-type (DS138), kip3$\Delta$ (DS613), dyn$\Delta$ (DS749), kip3-20(ts) dyn1Δ (DS765), kar3Δ102 (DS750), and kip3-30(ts) kar3Δ (DS752) were incubated at 23° C. for 2 d in liquid YPD medium. Approximately $10^4$ cells were spotted on solid YPD medium containing 1% DMSO and benomyl at the indicated concentration, and photographed after 3 d of growth at the indicated temperature.). This suggests that altered microtubule polymerization in the double mutant is a contributing factor to the synthetic lethality.

Figure 1B:
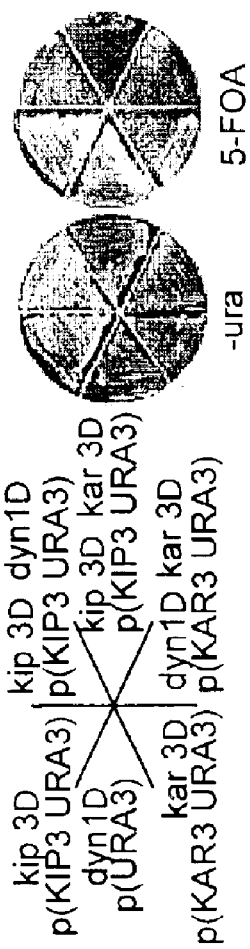
Figure 1C:
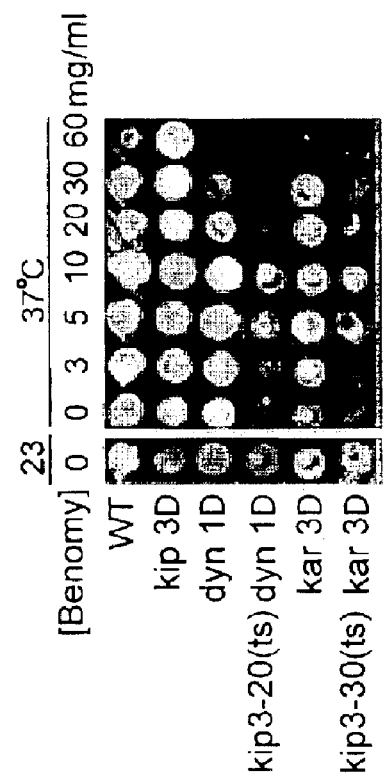

As noted above, the plasmid shuffle technique was also used to isolate a temperature-conditional kip3 and kar3 double mutant (FIG. 1B, above). Like the kip3(ts) dyn1Δ double mutant, lethality of the kip3-30(ts) kar3 double mutant was partially suppressed on medium containing a low concentration of benomyl (FIG. 1C, above). It was also noted that the kar3 and dyn1 double mutant was synthetically lethal (FIG. 1A, above), requiring a complementing plasmid for viability Conclusion Synthetic Lethality and Functional Overlap Testing for synthetic lethalitybetween the kip3 mutation and mutations in the DYN1 gene and each of the kinesin-related genes revealed that kip3 is synthetically lethal with either dyn1 or kar3. Since no single detectable defect in the kip3 dyn1 double mutant appears to account for the synthetic lethality, it is suspected that the synthetic lethality is caused by the cumulative effect of partial defects in sequential movements. A similar conclusion is suggested by the morphology of the kip3 kar3 conditional double mutant, which essentially exhibits a superimposition of the defects observed in the single mutants.

Although the foregoing invention has been described in some detail for purposes of clarity of understanding, it will be apparent that certain changes and modifications may be practiced within the scope of the appended claims. Therefore, the present embodiments are to be considered as illustrative and not restrictive, and the invention is not to be limited to the details given herein, but may be modified within the scope and equivalents of the appended claims. All publications, patents, and patent applications cited herein are hereby incorporated by reference in their entirety for all purposes.

What is claimed is:

1. A method for identifying a compound having antifungal activity, the method comprising:
   (a) providing a population of double mutant fungal cells, the cells having genetic mutations of at least a first and a second gene wherein (1) the genes encode motor proteins that have antagonistic and complementary functions; (2) the mutation of said first gene or said second gene results in loss of function of the protein encoded thereby, but does not prevent cellular proliferation; and (3) mutation of said first and second genes results in the loss of function of both proteins encoded thereby and prevents proliferation under restrictive conditions;
   (b) incubating the mutant fungal cells under a restrictive condition where the genetic mutations inhibit growth of the cells;
   (c) contacting the mutant fungal cells with a test compound under the restrictive condition; and
   (d) determining whether the test compound allows proliferation of the mutant fungal cells under the restrictive conditions, indicating the test compound relieves the effects of at least one of the mutations and is a potential antifungal agent.

2. The method of claim 1, further comprising the steps of:
   (e) providing a second population of fungal cells having normal microtubule stability;
   (f) incubating the second population of fungal cells under growth conditions;
   (g) contacting the second population with the potential antifungal agent identified in step (d);
   (h) determining whether the potential antifungal agent inhibits growth of the second population, indicating that the potential antifungal agent is an antifungal agent.

3. The method of claim 2, wherein the second population of fungal cells is the same species as the mutant fungal cells.

4. The method of claim 1, wherein the mutant fungal cells are of a genus selected from the group consisting of *Aspergillus, Saccharomyces, Cryptococcus, Histoplasma*, and *Candida*.

5. The method of claim 1, wherein the genetic mutations hyper-stabilize microtubules.

6. The method of claim 1, wherein the determining step comprises a method of detection selected from the group consisting of absorbance spectrophotometry, fluorescence spectroscopy, fluorescence microscopy, epifluorescence microscopy, light microscopy, phosphorimaging and nephelemetry.

7. The method of claim 6, wherein the determining step further comprises a staining of the mutant fungal cells to aid in detection.

8. The method of claim 7, wherein the staining is performed with a dye selected from the group consisting of a fluorogenic compound, a naturally fluorescent compound, a calorimetric compound, a chemiluminescent compound, a radioactive compound and combinations thereof.

9. The method of claim 1, wherein a plurality of test compounds are assayed in parallel.

10. The method of claim 1, further comprising the steps of:
    (e) providing a population of host cells selected from the group consisting of mammalian cells and plant cells;
    (f) incubating the cells under growth conditions;
    (g) contacting the cells with the potential antifungal agent identified in step (d);
    (h) determining whether the potential antifungal agent inhibits growth of the cells indicating that the potential antifungal agent is toxic to host cells.

11. The method of claim 10, wherein the potential antifungal agent does not inhibit growth the host cells.

12. The method of claim 11, wherein the potential antifungal agent is an antifungal therapeutic.

13. The method of claim 11, wherein the host cells are human cells.

14. A method for identifying a compound having antifungal activity, the method comprising:
    (a) providing a population of double mutant fungal cells, the cells having genetic mutations of at least a first and a second gene wherein (1) the genes encode motor proteins that have antagonistic and complementary functions; (2) the mutation of said first gene or said second gene results in loss of function of the protein encoded thereby, but does not prevent cellular proliferation; and (3) mutation of said first and second genes results in the loss of function of both proteins encoded thereby and prevents proliferation under restrictive conditions;

(b) incubating the mutant fungal cells under a restrictive condition where the genetic mutations inhibit growth of the cells;

(c) contacting the mutant fungal cells with a test compound under the restrictive condition; and (d) determining whether the test compound allows proliferation of the mutant fungal cells under the restrictive conditions, indicating the test compound relieves the effects of at least one of the mutations and is a potential antifungal agent;

(e) providing a second population of fungal cells having normal microtubule stability, wherein the second population of fungal cells is a different species from the mutant fungal cells;

(f) incubating the second population of fungal cells under growth conditions;

(g) contacting the second population with the potential antifungal agent identified in step (d);

(h) determining whether the potential antifungal agent inhibits growth of the second population, indicating that the potential antifungal agent is an antifungal agent.

15. The method of claim 14, wherein the mutant fungal cells are of a genus selected from the group consisting of *Aspergillus, Saccharomyces, Cryptococcus, Histoplasma*, and *Candida*.

16. The method of claim 14, wherein the genetic mutations hyper-stabilize microtubules.

17. The method of claim 14, wherein the mutated genes comprise a tubulin-related gene and dynein gene.

18. The method of claim 17, wherein the mutant fungal cells are *Saccharomyces cerevisiae* and the mutated genes comprise kip3 and dyn1 mutants.

19. The method of claim 17, wherein the mutant fungal cells are *Saccharomyces cerevisiae* and the mutated genes comprise kar3 and dyn1 mutants.

20. The method of claim 14, wherein the mutated genes comprise two kinesin-related genes.

21. The method of claim 20, wherein the mutant fungal cells are *Saccharomyces cerevisiae* and the mutated genes comprise kip3 and kar3 mutants.

22. The method of claim 14, wherein the determining step comprises a method of detection selected from the group consisting of absorbance spectrophotometry, fluorescence spectroscopy, fluorescence microscopy, epifluorescence microscopy, light microscopy, phosphorimaging and nephelemetry.

23. The method of claim 22, wherein the determining step further comprises a staining of the mutant fungal cells to aid in detection.

24. The method of claim 23, wherein the staining is performed with a dye selected from the group consisting of a fluorogenic compound, a naturally fluorescent compound, a calorimetric compound, a chemiluminescent compound, a radioactive compound and combinations thereof.

25. The method of claim 14, wherein a plurality of test compounds are assayed in parallel.

26. The method of claim 14, further comprising the steps of:

(i) providing a population of host cells selected from the group consisting of mammalian cells and plant cells;

(j) incubating the cells under growth conditions;

(k) contacting the cells with the potential antifungal agent identified in step (d);

(l) determining whether the potential antifungal agent inhibits growth of the cells indicating that the potential antifungal agent is toxic to host cells.

27. The method of claim 26, wherein the potential antifungal agent does not inhibit growth the host cells.

28. The method of claim 27, wherein the potential antifungal agent is an antifungal therapeutic.

29. The method of claim 27, wherein the host cells are human cells.

30. A method for identifying a compound having antifungal activity, the method comprising:

(a) providing a population of double mutant fungal cells, the cells having genetic mutations of at least a first and a second gene wherein the mutated genes comprise a tubulin-related gene and dynein gene;

(b) incubating the mutant fungal cells under a restrictive condition where the genetic mutations inhibit growth of the cells;

(c) contacting the mutant fungal cells with a test compound under the restrictive condition; and (d) determining whether the test compound allows proliferation of the mutant fungal cells under the restrictive conditions, indicating the test compound relieves the effects of at least one of the mutations and is a potential antifungal agent.

31. The method of claim 30, wherein the mutant fungal cells are *Saccharomyces cerevisiae* and the mutated genes comprise kip3 and dyn1 mutants.

32. The method of claim 30, wherein the mutant fungal cells are *Saccharomyces cerevisiae* and the mutated genes comprise kar3 and dyn1 mutants.

33. The method of claim 30, wherein the mutant fungal cells are of a genus selected from the group consisting of *Aspergillus, Saccharomyces, Cryptococcus, Histoplasma*, and *Candida*.

34. The method of claim 30, wherein the determining step comprises a method of detection selected from the group consisting of absorbance spectrophotometry, fluorescence spectroscopy, fluorescence microscopy, epifluorescence microscopy, light microscopy, phosphorimaging and nephelemetry.

35. The method of claim 34, wherein the determining step further comprises a staining of the mutant fungal cells to aid in detection.

36. The method of claim 35, wherein the staining is performed with a dye selected from the group consisting of a fluorogenic compound, a naturally fluorescent compound, a calorimetric compound, a chemiluminescent compound, a radioactive compound and combinations thereof.

37. The method of claim 30, wherein a plurality of test compounds are assayed in parallel.

38. The method of claim 30, further comprising the steps of:

(e) providing a population of host cells selected from the group consisting of mammalian cells and plant cells;

(f) incubating the cells under growth conditions;

(g) contacting the cells with the potential antifungal agent identified in step (d);

(h) determining whether the potential antifungal agent inhibits growth of the cells indicating that the potential antifungal agent is toxic to host cells.

39. The method of claim 38, wherein the potential antifungal agent does not inhibit growth the host cells.

40. The method of claim 39, wherein the potential antifungal agent is an antifungal therapeutic.

41. The method of claim 39, wherein the host cells are human cells.

42. A method for identifying a compound having antifungal activity, the method comprising:
   (a) providing a population of double mutant fungal cells, the cells having genetic mutations of at least a first and a second gene wherein the mutated genes comprise two kinesin-related genes;
   (b) incubating the mutant fungal cells under a restrictive condition where the genetic mutations inhibit growth of the cells;
   (c) contacting the mutant fungal cells with a test compound under the restrictive condition; and
   (d) determining whether the test compound allows proliferation of the mutant fungal cells under the restrictive conditions, indicating the test compound relieves the effects of at least one of the mutations and is a potential antifungal agent.

43. The method of claim 42, wherein the mutant fungal cells are *Saccharomyces cerevisiae* and the mutated genes comprise kip3 and kar3 mutants.

44. The method of claim 42, wherein the mutant fungal cells are of a genus selected from the group consisting of *Aspergillus, Saccharomyces, Cryptococcus, Histoplasma,* and *Candida*.

45. The method of claim 42, wherein the determining step comprises a method of detection selected from the group consisting of absorbance spectrophotometry, fluorescence spectroscopy, fluorescence microscopy, epifluorescence microscopy, light microscopy, phosphorimaging and nephelometry.

46. The method of claim 45, wherein the determining step further comprises a staining of the mutant fungal cells to aid in detection.

47. The method of claim 46, wherein the staining is performed with a dye selected from the group consisting of a fluorogenic compound, a naturally fluorescent compound, a calorimetric compound, a chemiluminescent compound, a radioactive compound and combinations thereof.

48. The method of claim 42, wherein a plurality of test compounds are assayed in parallel.

49. The method of claim 42, further comprising the steps of:
   (e) providing a population of host cells selected from the group consisting of mammalian cells and plant cells;
   (f) incubating the cells under growth conditions;
   (g) contacting the cells with the potential antifungal agent identified in step (d);
   (h) determining whether the potential antifungal agent inhibits growth of the cells indicating that the potential antifungal agent is toxic to host cells.

50. The method of claim 49, wherein the potential antifungal agent does not inhibit growth the host cells.

51. The method of claim 50, wherein the potential antifungal agent is an antifungal therapeutic.

52. The method of claim 50, wherein the host cells are human cells.

53. A method for identifying a compound having antifungal activity, the method comprising:
   (a) providing a population of double mutant fungal cells, the cells having genetic mutations of at least a first and a second gene wherein (1) the genes encode motor proteins that have antagonistic and complementary functions; (2) the mutation of said first gene or said second gene results in loss of function of the protein encoded thereby, but does not prevent cellular proliferation; and (3) mutation of said first and second genes results in the loss of function of both proteins encoded thereby and prevents proliferation under restrictive conditions;
   (b) incubating the mutant fungal cells under a restrictive condition where the genetic mutations inhibit growth of the cells;
   (c) contacting the mutant fungal cells with a test compound under the restrictive condition; and
   (d) determining whether the test compound allows proliferation of the mutant fungal cells under the restrictive conditions, indicating the test compound relieves the effects of at least one of the mutations and is a potential antifungal agent;
   (e) providing a second population of mutant fungal cells with the genetic mutations;
   (f) incubating the mutant fungal cells under a restrictive condition where the genetic mutations inhibits growth;
   (g) contacting the mutant fungal cells with a known microtubule destabilizing compound under the restrictive condition; and
   (h) determining whether proliferation of the mutant fungal cells in the presence of the test compound is about equal to or greater than proliferation in the presence of the known microtubule destabilizing compound, indicating the test compound is an effective microtubule destabilizer.

54. The method of claim 53, wherein the microtubule destabilizer is a nocodazole-like compound.

55. The method of claim 54, wherein the microtubule destabilizer is benomyl.

56. The method of claim 53, wherein the mutant fungal cells are of a genus selected from the group consisting of *Aspergillus, Saccharomyces, Cryptococcus, Histoplasma,* and *Candida*.

57. The method of claim 53, wherein the genetic mutations hyper-stabilize microtubules.

58. The method of claim 53, wherein the mutated genes comprise a tubulin-related gene and dynein gene.

59. The method of claim 58, wherein the mutant fungal cells are *Saccharomyces cerevisiae* and the mutated genes comprise kip3 and dyn1 mutants.

60. The method of claim 58, wherein the mutant fungal cells are *Saccharomyces cerevisiae* and the mutated genes comprise kar3 and dyn1 mutants.

61. The method of claim 53, wherein the mutated genes comprise two kinesin-related genes.

62. The method of claim 61, wherein the mutant fungal cells are *Saccharomyces cerevisiae* and the mutated genes comprise kip3 and kar3 mutants.

63. The method of claim 53, wherein the step of determining whether the test compound allows proliferation comprises a method of detection selected from the group consisting of absorbance spectrophotometry, fluorescence spectroscopy, fluorescence microscopy, epifluorescence microscopy, light microscopy, phosphorimaging and nephelometry.

64. The method of claim 63, wherein the step of determining whether the test compound allows proliferation further comprises a staining of the mutant fungal cells to aid in detection.

65. The method of claim 64, wherein the staining is performed with a dye selected from the group consisting of a fluorogenic compound, a naturally fluorescent compound, a calorimetric compound, a chemiluminescent compound, a radioactive compound and combinations thereof.

66. The method of claim 53, wherein a plurality of test compounds are assayed in parallel.

67. The method of claim 53, further comprising the steps of:
- (i) providing a population of host cells selected from the group consisting of mammalian cells and plant cells;
- (j) incubating the cells under growth conditions;
- (k) contacting the cells with the potential antifungal agent identified in step (d);
- (l) determining whether the potential antifungal agent inhibits growth of the cells indicating that the potential antifungal agent is toxic to host cells.

68. The method of claim 67, wherein the potential antifungal agent does not inhibit growth the host cells.

69. The method of claim 68, wherein the potential antifungal agent is an antifungal therapeutic.

70. The method of claim 68, wherein the host cells are human cells.

* * * * *